United States Patent [19]
Samson et al.

[11] Patent Number: 5,549,109
[45] Date of Patent: Aug. 27, 1996

[54] SHEATHED MULTIPOLAR CATHETER AND MULTIPOLAR GUIDEWIRE FOR SENSING CARDIAC ELECTRICAL ACTIVITY

[75] Inventors: Gene Samson, Milpitas; Gabriel B. Vegh, Alamo; Duane Dickens, Fremont; Herbert G. Rettke, Mountain View, all of Calif.

[73] Assignee: Target Therapeutics, Inc., Fremont, Calif.

[21] Appl. No.: 353,529

[22] Filed: Dec. 8, 1994

Related U.S. Application Data

[63] Continuation of Ser. No. 130,635, Oct. 1, 1993, abandoned.

[51] Int. Cl.$^6$ ............................................. A61B 5/042
[52] U.S. Cl. ............................................. 128/642
[58] Field of Search ..................... 128/642; 607/116, 607/122

[56] References Cited

U.S. PATENT DOCUMENTS

| | | | |
|---|---|---|---|
| Re. 33,925 | 5/1992 | Bales et al. ............... | 606/48 |
| 452,220 | 5/1891 | Gunning . | |
| 3,423,772 | 1/1969 | Lurie et al. ............... | 128/642 |
| 3,760,812 | 9/1975 | Timm et al. ............... | 607/116 |
| 4,271,847 | 6/1981 | Stokes ....................... | 128/786 |
| 4,332,259 | 6/1982 | McCorkle, Jr. ........... | 128/786 |

(List continued on next page.)

FOREIGN PATENT DOCUMENTS

| | | |
|---|---|---|
| 0249338A3 | 12/1987 | European Pat. Off. . |
| 0293499 | 12/1988 | European Pat. Off. . |
| 0369044 | 5/1990 | European Pat. Off. . |
| 1813232 | 6/1969 | Germany . |
| 2605590 | 8/1977 | Germany . |
| 3517732A1 | 11/1986 | Germany . |
| 3718139C1 | 12/1988 | Germany . |
| WO80/02801 | 12/1980 | WIPO . |
| WO90/03151 | 5/1990 | WIPO . |
| WO92/21278 | 10/1992 | WIPO . |
| WO93/08869 | 5/1993 | WIPO . |
| WO93/08756 | 5/1993 | WIPO . |
| WO93/08757 | 5/1993 | WIPO . |
| WO93/08755 | 5/1993 | WIPO . |
| WO94/06349 | 3/1994 | WIPO . |
| WO94/16618 | 8/1994 | WIPO . |

OTHER PUBLICATIONS

Pedro Brugada, et al., "Transcoronary Chemical Ablation of Ventricular Tachycardia", Circ., vol. 79, No. 3, Mar. 1989, pp. 475–482.

Angelo A. V. DePaola, et al., "Transcoronary Chemical Ablation of Ventricular Tachycardia in Chronic Chagasic Myocarditis", JACC, vol. 20, No. 2, Aug. 1992, pp. 480–482.

John D. Fisher et al., "Nonsurgical Electrical Ablation of Tachycardias: Importance of Prior in Vitro Testing of Catheter Leads", PACE, vol. 7, Jan.–Feb. 1984, pp. 74–81.

(List continued on next page.)

Primary Examiner—William E. Kamm
Attorney, Agent, or Firm—Crosby, Heafey, Roach & May

[57] ABSTRACT

This invention is a medical device. It is a multipolar catheter assembly optionally in combination with a guidewire. Each of the catheter and the guidewire may be sheathed and have multiple electrodes at their distal ends. Because of their size and flexibility, the catheter and the guidewire may be used at virtually any point within the vasculature particularly, however, within the cardiac arteries or veins, perhaps in conjunction with external electrocardiogram leads, to map the body's electrical activity. When used in the heart, they may be used to determine the source of a cardiac arrythmia. The intimate presence of the guidewire or catheter body in the cardiac vasculature allows the response time to changes in cardiac electrical activity is very quick. The invention is also a method for mapping the electrical activity of the heart by use of one or more of these inventive guidewires or catheters in the cardiac arteries or veins. They may also be used to determine the local electrical activity of any site within the body, such as in the brain.

23 Claims, 8 Drawing Sheets

U.S. PATENT DOCUMENTS

| | | | |
|---|---|---|---|
| 4,402,330 | 9/1983 | Lindemans | 128/786 |
| 4,437,474 | 3/1984 | Peers-Trevarton | 128/784 |
| 4,449,528 | 5/1984 | Auth et al. | 128/303.1 |
| 4,458,677 | 7/1984 | McCorkle, Jr. | 128/786 |
| 4,481,953 | 11/1984 | Gold et al. | 128/786 |
| 4,505,982 | 3/1985 | Hoheisel . | |
| 4,546,141 | 10/1985 | Gebauer . | |
| 4,556,589 | 12/1985 | Neumann et al. . | |
| 4,559,951 | 12/1985 | Dahl et al. | 128/642 |
| 4,658,836 | 4/1987 | Turner | 128/642 |
| 4,670,503 | 6/1987 | Neumann et al. . | |
| 4,690,155 | 9/1987 | Hess | 128/786 |
| 4,739,768 | 4/1988 | Engelson . | |
| 4,777,955 | 10/1988 | Brayton et al. | 128/642 |
| 4,785,815 | 11/1988 | Cohen . | |
| 4,829,116 | 5/1989 | Piesold . | |
| 4,840,186 | 6/1989 | Lekholm et al. | 607/116 |
| 4,867,173 | 9/1989 | Leoni | 128/772 |
| 4,869,248 | 9/1989 | Narula | 128/303.13 |
| 4,933,388 | 6/1990 | Blickle et al. . | |
| 4,945,912 | 8/1990 | Langberg | 128/642 |
| 4,955,382 | 9/1990 | Franz et al. | 128/642 |
| 4,957,110 | 9/1990 | Vogel et al. | 128/642 |
| 4,966,597 | 10/1990 | Cosman | 606/50 |
| 4,979,510 | 12/1990 | Franz | 128/786 |
| 4,979,799 | 12/1990 | Herbrechtsmeier et al. . | |
| 4,984,870 | 1/1991 | Herbrechtsmeier et al. . | |
| 4,986,630 | 1/1991 | Herbrechtsmeier et al. . | |
| 4,991,932 | 2/1991 | Herbrechtsmeier et al. . | |
| 5,029,585 | 7/1991 | Lieber et al. | 128/642 |
| 5,044,375 | 9/1991 | Bach, Jr. et al. | 128/786 |
| 5,056,517 | 10/1991 | Fenici . | |
| 5,083,565 | 1/1992 | Parins | 128/642 |
| 5,095,916 | 3/1992 | Smits | 128/784 |
| 5,095,917 | 3/1992 | Vancaillie | 128/831 |
| 5,099,838 | 3/1992 | Bardy | 128/419 D |
| 5,104,393 | 4/1992 | Isner et al. | 606/15 |
| 5,122,136 | 6/1992 | Guglielmi et al. | 606/32 |
| 5,125,896 | 6/1992 | Hojeibane | 604/95 |
| 5,140,987 | 8/1992 | Schuger et al. | 128/642 |
| 5,154,175 | 10/1992 | Gunther | 128/642 |
| 5,163,445 | 11/1992 | Christian et al. | 128/785 |
| 5,165,403 | 11/1992 | Mehra | 128/419 D |
| 5,165,975 | 11/1992 | Goshiki | 428/36.4 |
| 5,170,802 | 12/1992 | Mehra | 128/784 |
| 5,172,699 | 12/1992 | Svenson et al. | 128/705 |
| 5,174,288 | 12/1992 | Bardy et al. | 128/419 D |
| 5,184,621 | 2/1993 | Vogel et al. | 128/642 |
| 5,193,546 | 3/1993 | Shaknovich | 128/662.06 |
| 5,193,550 | 3/1993 | Duffin | 128/697 |
| 5,215,103 | 6/1993 | Desai | 128/784 |
| 5,330,522 | 7/1994 | Kreyenhagen | 607/122 |
| 5,364,352 | 11/1994 | Cimino et al. | 604/95 |

OTHER PUBLICATIONS

Alden H. Harken, "Surgical Treatment of Cardiac Arrhythmias", *Scientific American,* Jul. 1993, pp. 68–74.

Keiichi Hashimoto, et al., "Significance of S–T Segment Elevations in Acute Myocardial Ischemia", *The Am. Journal of Card.,* vol. 37, Mar. 31, 1976, pp. 493–500.

Hiroshi Inoue, et al., "Intracoronary Ethyl Alcohol or Phenol Injection Ablates Aconitine–Induced Ventricular Tachycardia in Dogs", *JACC,* vol. 10, No. 6, Dec. 1987, pp. 1342–1349.

Michael D. Lesh, et al., "Mapping in the Right Cornonary Artery as an Aid to Radiofrequency Ablation of Right–Sided Accessory Pathways", *PACE,* vol. 14, NASPE Abstracts, Apr. 1991, Part II, p. 671.

Verna E. Repetto et al., "Transcoronary Epicardial Mapping of Accessory Pathways. Implications for Ablation Techniques", 10th International Congress The New Frontiers of Arrhythmias, Marilleva, Italy, Jan. 25–Feb. 1, 1992.

John Swartz, et al., "Endocardial Atrial Catheter Ablation of Accessory Pathways After Intravascular Localization", *PACE,* vol. 13, NASPE Abstracts, Apr. 1990, p. 527.

Tibor S. Szabo, et al., "Localization of Accessory Pathways in the Wolff–Parkinson–White Syndrome", *PACE,* vol. 12, Oct. 1989, pp. 1691–1705.

Lawrence T. Weston et al., "A Prototype Coronary Electrode Catheter for Intracoronary Electrogram Recording", *American Journal of Cardiology,* vol. 70 Dec. 1, 1992, pp. 1492 and 1493.

Michael Haissaguerre, M.D., et al., "Closed–Chest Ablation of Retrograde Conduction in Patients with Atrioventricular Nodal Reentrant Tachycardia", *The New England Journal of Medicine,* vol. 320, No. 7, Feb. 16, 1989, pp. 426–433.

Melvin M. Scheinman, M.D., "Catheter Techniques for Ablation of Supraventricular Tachycardia", *The New England Journal of Medicine,* vol. 320, No. 7, Feb. 16, 1989, pp. 460–461.

United States Catheter & Instrument Corporation Advertisement "Tripolar His Bundle Electrodes"2 pp. Oct. 1971.

6.170    20msec

SHEATHED MULTIPOLAR CATHETER AND MULTIPOLAR GUIDEWIRE FOR SENSING CARDIAC ELECTRICAL ACTIVITY

This is a continuation of application Ser. No. 08/130,635 which was filed on Oct. 1, 1993, now abandoned.

FIELD OF THE INVENTION

This invention is a medical device. It is a multipolar catheter assembly optionally in combination with a guidewire. Each of the catheter and the guidewire may be sheathed, especially with a fluoropolymeric composition comprising tetrafluoroethylene, hexafluoropropylene, and vinylidene fluoride, and have multiple electrodes at their distal ends. Because of their size and flexibility, the catheter and the guidewire may be used at virtually any point within the vasculature particularly, however, within the cardiac arteries or veins, perhaps in conjunction with external electrocardiogram leads, to map the body's electrical activity. When used in the heart, they may be used to determine the source of a cardiac arrythmia. The intimate presence of the guidewire or catheter body in the cardiac vasculature allows the response time to changes in cardiac electrical activity is very quick.

The invention is also a method for mapping the electrical activity of the heart by use of one or more of these inventive guidewires or catheters in the cardiac arteries or veins. They may also be used to determine the local electrical activity of any site within the body, such as in the brain.

BACKGROUND OF THE INVENTION

The heartbeat is caused by the rhythmic and orderly contraction of heart chambers surrounded by heart muscles. The normal heartbeat starts with the contraction of the atria (atrial systole) followed by contraction of the ventricles (ventricular systole) while the atria are in atrial diastole. During the following diastole, all four chambers are sequentially relaxed.

The heartbeat originates in a cardiac conduction system made up of the sinoatrial node (SA node), the internodal atrial pathways, the atrioventricular node (AV node), the Bundle of His and its various branches, and the Purkinje system. The Bundle of His conduction system spreads the heartbeat to the apex of the myocardium. The SA node typically discharges more quickly than the other portions of the system. Acting as a natural cardiac pacemaker, the SA node discharge rate generally determines the rate at which the heart beats. The impulses generated in the SA node pass through the atrial pathways to the AV node, to the Bundle of His and thence to its branches and the ventricular muscle through the Purkinje system. However, the various parts of the conduction system and the myocardium itself are capable of spontaneous discharge. The various portions of the conduction system are mostly striate, modified cardiac muscle having less than distinct boundaries.

Normally, the human heart rate is about 70 beats per second at rest. That rate is accelerated (tachycardia) by exercise, fever, and the like; the rate is slowed (brachycardia) during sleep. Other normal physical causes, e.g., breathing, cause a variation in heart rate.

There are abnormal fluctuations in the heart rate. For instance, disease may cause the so-called natural pacemaker function to shift from the SA node to the AV node. Other diseases lower the membrane potential of atrial and ventricular muscle fibers causing them to discharge repetitively. Ectopic foci of excitation of the His-Purkinje fibers result in either extrasystole (or premature beat) if the ectopic focus discharges before the expected beat or in atrial flutter (paroxysural tachycardia) if the focus repetitively discharges at a rate higher than the rate of the SA node.

These and other arrhythmias may cause benign or severe effects. Although arrythmia such as paroxysmal ventricular tachycardia are often benign, they are sometimes associated with ventricular fibrillation. Ventricular fibrillation, in which the ventricular muscle fibers contract irregularly, cause the heart to pump blood very inefficiently. The resultant serious decline in cardiac output, if untreated, is often fatal.

Control of arrhythmia is undertaken in a variety of ways. Antiarrhythmic drugs often slow conduction in the conduction system and the myocardium. Some block $Na^+$, $Ca^{++}$ channels or $\beta$-adrenergic activity in the heart. These treatments are effective in clinical situations but often must be continued for extended periods of time.

Another method for controlling arrhythmia, particularly tachycardia, short of open heart surgery to surgically section the Bundle of His, is via the use of an ablation catheter. These devices are used to ablate cardiac conduction pathways.

One such device is shown in U.S. Pat. No. 4,785,815, to Cohen. Cohen shows a catheter which is inserted in typical fashion into a chamber of the heart (preferably entering the body remotely through the femoral artery) so that the distal end of the catheter may be positioned against the heart wall in close proximity to one of the cardiac conduction pathways. The catheter carries detectors for sensing various electrical potentials within the heart, e.g., the HRA (high right atrium), the HBE (His Bundle electrogram), and the VA (ventricular apex). The distal end of the catheter also carries the termination of a laser optical conduit. The laser is used to ablate the offending conduction pathway tissue. Lasering of the chosen pathway is carried out until the monitored cardiac activity is properly modified, e.g., when the Bundle of His is ablated, the surgeon notes that the atrial and ventricular activity have become asynchronous.

U.S. Pat. No. 5,056,517, to Fenici, discloses a cardiac electrocatheter optionally containing ablation wires, fiber optics, and distal and proximal electrodes for intracardial mapping.

For these and a variety of other indications, accurate mapping of cardiac electrical activity is desirable. Increasingly, the mapping of that activity is desirably more and more precise. For instance, choice of pacemaker type, proper placement of pacemaker leads, and proper programming of pacemaker variables depends in large measure upon the coronary malady to be corrected. Indeed, implantable pacemakers have been provided with an internationally adopted 4 or 5-letter code specifying which of the thousands of combinations of electrical sensing, pacing, inhibiting, etc., activities the specific pacemaker may undertake. For instance, the pacemaker chosen for a patient with acute inferior myocardial infarction is quite different from that chosen for a patient with acute anterior myocardial infarction and those likely will be quite different from pacemakers chosen for an aberrant physiological reflex such as carotid sinus hypersensitivity. In each instance, the cardiac electrical activity is different; in each case the need to properly assess the activity and then either to inhibit it or to enhance it so to restore cardiac muscle activity to a normal and proper rate is obvious to all who take the time to consider it.

Classically, electrocardiography is often undertaken non-invasively from outside the body by leads placed at specific positions on the body. Observation of the resulting signals provides preliminary information relating to cardiac electrical activity. Additional information has been achieved via use of invasive sensors such as that shown in U.S. Pat. No. 5,056,517, noted above.

None of the sensors discussed above are said to be covered with the fluoropolymeric alloy described herein.

SUMMARY OF THE INVENTION

This invention is a catheter, having multiple electrical sensing poles or electrodes in the region of its distal end. The catheter may be used in conjunction with a guidewire either with or without multiple electrical sensing poles or electrodes in the region of its distal end. Central to this device is the use of a fluoropolymeric mixture or alloy of tetrafluoroethylene, hexafluoropropylene, and vinylidene fluoride as a sheath on the exterior of at least one of the catheter or the guidewire. The catheter, in conjunction with that guidewire, may be used for mapping coronary electrical activity in either or both of the coronary arteries or in coronary veins. As an optional aspect of the invention, the guidewire may be used with a vasoocclusive device, such as a vasoocclusive coil or braid, with or without interior or exterior ancillary fibrous material. In this optional variation, the guidewire may be used to occlude small coronary arteries or veins to remedy a detected arrhythmia even during the process of monitoring cardiac electrical activity. The inventive catheter body may be used to infuse diagnostic or therapeutic agents into the cardiac vasculature during use as a mapping tool and even while the guidewire is in place.

Simply described, the invention also includes a guidewire which has a braided or flat wound tube made up of individually insulated conductive wires or filaments. At the distal end of the guidewire the conductors are attached individually to sensor points or electrodes, which electrodes are spaced apart from each other. The woven braid may be woven about a wire core to provide some additional stiffness to the guidewire assembly. If desired, the guidewire may be so equipped as to introduce vasoocclusive devices at its distal end. At the proximal end of the guidewire assembly, an electrical junction, a socket or the like, may be installed to allow ready connection to an external monitoring device. At least a portion of the guidewire may be ensheathed with a previously, at least partially crosslinked, mixture or alloy of tetrafluoroethylene, hexafluoropropylene, and vinylidene fluoride. The fluoropolymer composition is preferably extruded into suitably sized tubing, at least partially cross-linked (often using radiation such as electron beam), placed about the guidewire, and heated to shrink the tubing into intimate contact with the guidewire.

The catheter is typically a multilayer assembly often having a number of coaxial polymeric tubes, the tubes may be separated by a braided or flat wound tube made up of individually insulated conductive wires or filaments. The tube may be made of a combination of conductive wires and other filamentary material, such as Dacron threads, to complete the tube when only a limited number of electrodes are needed. As with the guidewire, at the distal end of the catheter, the conductors are attached individually to sensor points or electrodes, which electrodes are spaced apart from each other. The braided or laid-up tube may be woven or laid-up tube about one or more inner polymeric tubing cores to provide structure to the catheter assembly. At the proximal end of the catheter assembly, an electrical junction, a socket or the like, may be installed to allow ready connection to an external monitoring device. Similarly to the guidewire, the areas of the catheter which do not constitute a sensor area may be covered with a fluoropolymer composition of tetrafluoroethylene, hexafluoropropylene, and vinylidene fluoride. It is preferably placed onto the catheter by first extruding the polymeric composition into suitably sized tubing, at least partially cross-linking the polymer (often using radiation such as electron beam), placing the polymer about the catheter, and heating the polymer to shrink it into intimate contact with the catheter body.

The guidewire and the catheter may be introduced from an external site such as the femoral artery or vein up through the mid portion of the body into the cardiac arteries or veins. There, the guidewire and the catheter may be placed in such a fashion that the local cardiac electrical activity within the cardiac muscle wall as monitored through the cardiac vein or artery wall may be measured and monitored. By choice of monitoring site throughout the coronary vasculature system, the electrical activity of the heart may be completely mapped. The guidewire and catheter may be used during these monitoring activities either in a bipolar mode, that is to say, using adjacent pairs of electrical contacts at their distal tip, or may be used in unipolar mode in conjunction with other electrodes suitably placed exterior or interior to the body or to the heart.

The use of the tetrafluoroethylene, hexafluoropropylene, and vinylidene fluoride composition on either or both of the sensing guidewire and catheter accentuates the control the attending physician has over the use of the combination in placement of the sensors and in detection of cardiac abnormalities.

DESCRIPTION OF THE INVENTION

As was noted above, this invention is a medical device. Specifically, the invention is a catheter, optionally containing a guidewire, suitable for monitoring electrical activity interior to the body. The optional guidewire may be a typical guidewire or may have multiple poles or electrodes on its distal end. Central to this device is the use of a fluoropolymeric mixture or alloy of tetrafluoroethylene, hexafluoropropylene, and vinylidene fluoride as a sheath on the exterior of at least one of the catheter or the guidewire.

One important aspect of this invention is the monitoring of cardiac electrical activity by placement of the catheter's (and optionally, the guidewire's) multiple contacts in cardiac veins or in the cardiac arteries. Because of the size and flexibility of this device, it is suitable for monitoring other sources of electrical activity within the human or animal body.

Catheter Structure

Figure 1:
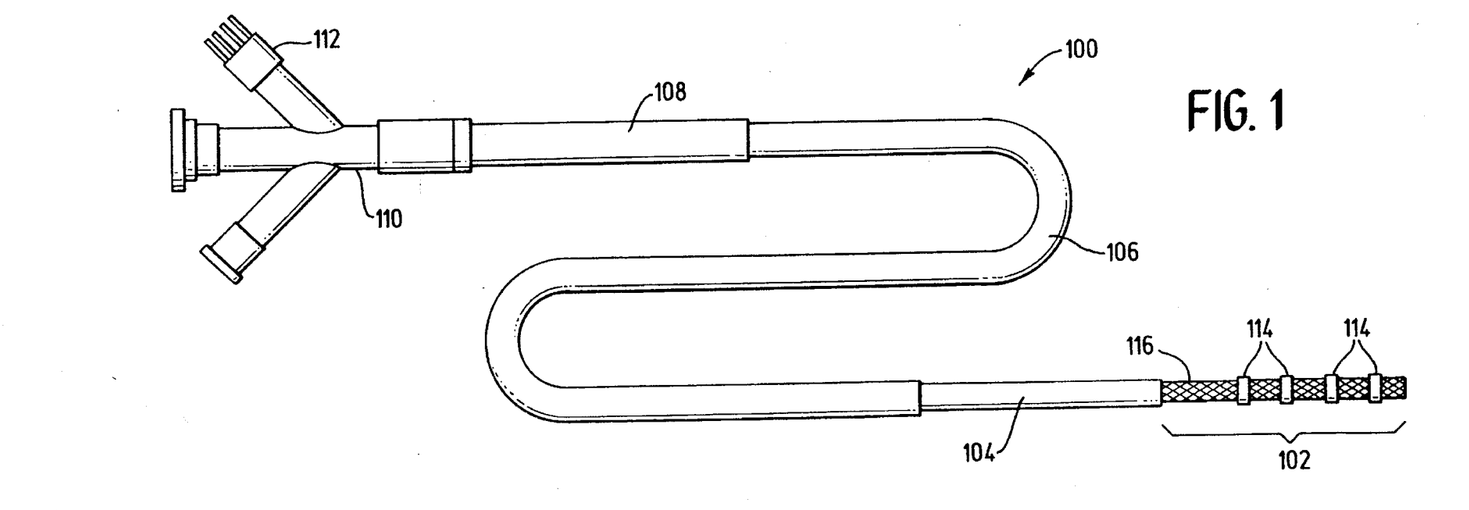
FIG. 1 is an side view of the inventive multipolar catheter assembly.

FIG. 1 shows a side view of a catheter (100) made according to this invention. The depiction in the figure is a typical configuration using the concept of sections having multiple flexibility generally as described in U.S. Pat. No. 4,739,768, to Engelson, but is not limited to the specifics of that patent.

Catheter (100) is made is an elongate tube often between 50 and 300 cm. in length and is made up of the following portions: a sensor section (102), a distal section (104) just proximal of the sensor section (102), a mid section (106), and a proximal section (108). The catheter has a lumen extending axially from the most proximal portion of the catheter (100) to the distal end of the sensor section (102). A proximal fitting (110) for passage of the guidewire through the catheter lumen and having a sidearm for introduction of fluids into the catheter may also be employed. An electrical connector (112) for connection to the electrodes (114) through the wires of the wire tube (116) is also desirable.

Figure 2:
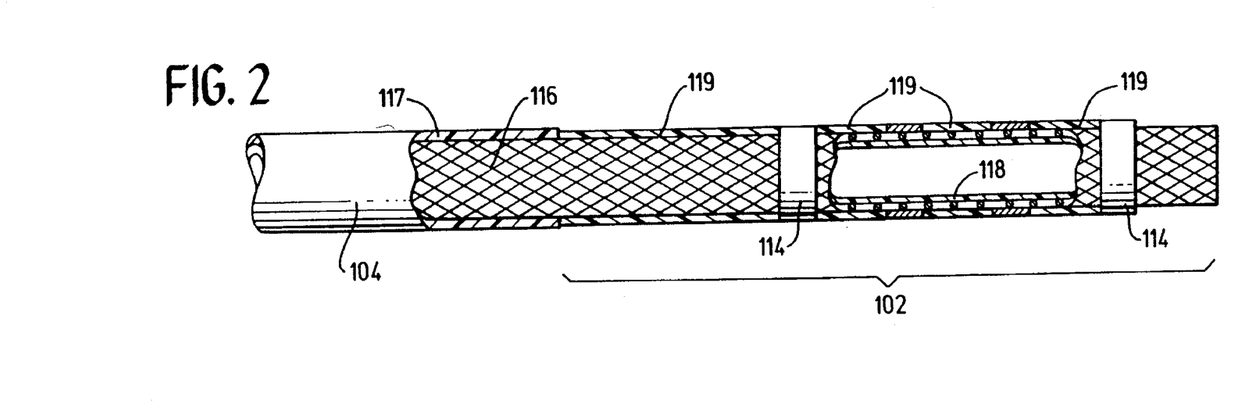
FIG. 2 is an enlarged, cutaway, side view of the distal section of the multipolar catheter assembly.

The sensor section (102) is shown on more detail in FIG. 2 but generally is a tube (116) of insulated wire or other filamentary material which has either been woven or flat wound usually over (and consequently is concentric with) a polymeric tube to provide an open lumen in that section. As will be described below in additional detail, the tube may be made up of a sufficient number of wires to allow connection to electrodes (114) of an appropriate number for the task involved. For instance, when mapping the electrical activity in the somewhat short circumflex artery, only a fairly short sensor section (102) with a few electrodes is desirable. The catheter (100) in FIG. 1 is equipped with four electrodes (114) for just such a purpose. The electrodes (114) may be spaced as appropriate but, for electrodes which are about 0.010 in length, a spacing of 1 mm. to 1 cm. is acceptable. Here, since only a few electrodes are involved, only a few insulated wires would be incorporated into the wire tube (116). The remainder of the filaments to complete the filamentary tube (116) could be Dacron, nylon, silk, or other appropriate natural or synthetic material. The number of electrodes may be any number but is at least one. We have found that a practical upper limit of the number of electrodes is sixteen, but that number is set only because of the difficulty of weaving very small insulated wires into a tube which retains sufficient flexibility to traverse the noted vasculature without causing trauma. Each electrode (114) preferably is attached to one wire in the wire tube (116) but such is not necessary.

Wire tube (116) extends from the sensor section (102) along the length of the catheter (100) to the proximal end and its connector (116).

The outer diameter of the electrodes (114) and the remainder of the sensor section (102) typically is between 0.030 and 0.100 inches but preferably is between 0.030 and 0.050 inches and most preferably is between 0.035 and 0.040 inches. The inner diameter of the sensor section (102) is sufficiently large to accommodate the guidewire used in the device but desirably provides about 0.002 to 0.005 inches of clearance between the guidewire and the tubing. For a 0.016 to 0.018 inch diameter guidewire, the inner diameter of the sensor section (102) would therefore be 0.018 to 0.023 inches.

Adjacent on the proximal end of the sensor section (102) is distal section (104). Distal section (104) is the most flexible of the three section (104), (104), and (106) and typically makes up 5 to 30% of the length of the catheter (100). This flexibility permits the catheter to track along a guidewire with ease into the various curves and loops it encounters in the human vasculature. It typically has a sheathing (117) made of a very soft material such as a silicone or a low density polyethylene or other suitable polymer. Especially preferred is a copolymer of tetrafluoroethylene, hexafluoropropylene, and vinylidene fluoride or an alloy or mixture of the three. It is preferably placed onto the catheter by first extruding the polymeric composition into suitably sized tubing, at least partially cross-linking the polymer (often using radiation such as electron beam), placing the polymer about the catheter, and heating the polymer to shrink it onto the wire tube (116) it surrounds. The wall thickness of the soft tubing making up distal section is preferably nominally 0.002".

Also within the scope of this invention is the placement of sheaths (119) of the polymeric tubing between the electrodes (114) and between the distal end of the distal section (104) and the electrodes. The sheathing (117) on the distal section (104) need not be of the same composition as that in the sensor section (102) although it is desirable to do so.

As is shown on FIG. 1, adjacent on the proximal end of the distal section (104) is mid section (106). Mid section (106) is the midway in flexibility between distal section (104) and proximal section (108) and typically makes up 5 to 30% of the length of the catheter (100). This section provides greater column strength in the distal regions of the catheter as it is moved along the tortuous path of the vasculature but with greater flexibility than the proximal section (108). This segment may be formed by extending the tubing found in the distal section (104) over and coaxial to a stiffer tubing composed of, e.g., polypropylene or high density polyethylene. It is within the scope of this invention that the mid section (106) and the proximal section (108) also be at least partially covered with a tubing of a copolymer of tetrafluoroethylene, hexafluoropropylene, and vinylidene fluoride or an alloy or mixture of the three as described above.

The proximal section (108) is the most stiff of the tubing sections and typically makes up 70 to 95% of the of the total length of the tubular member. Again, the section may be made by extending the tubing found in the distal section (104) and the outer surface of mid section (106) over and coaxial to a stiffer tubing composed of, e.g., polypropylene or high density polyethylene. As with the other sections, the inner diameter of the proximal section (108) should provide about 0.002 to 0.005 inches of clearance between the guidewire and the inner diameter of the tubing. For a 0.016 to 0.018 inch diameter guidewire, the inner diameter of the proximal section (108) would therefore be 0.018 to 0.023 inches. Choice of suitable, stiffer polymers to maintain the outer diameter at a relatively constant value, if such is desired, is within the ambit of one having ordinary skill in this art.

It is within the scope of this invention that the catheter (100) have sections of varying stiffness. Such a construction obviously may not entail discrete or quantum changes in the stiffness of the catheter body to occur. Additionally it is desired that the inner and/or outer surfaces of the catheter body be coated with a polymer to increase the lubricity of the catheter either with respect to the guidewire or with the lumen of the vasculature. Hydrophilic polymers such as polyvinylpyrrolidone, polyethylene oxide, and various acrylate-based polymers are suitable choices as hydrophilic polymers. Hydrophobic polymers such as polysulfones and polyfluoroalkanes are also suitable.

As noted above, we prefer to cover at least a portion of the sensor section (102), distal section (104), mid-section (106), or proximal section (108) with a fluoropolymeric composition comprising a copolymer of tetrafluoroethylene, hexafluoropropylene, and vinylidene fluoride or an alloy or mixture of the three. Especially suitable are the series of fluoroplastics known as "THV Fluoroplastics" produced by 3M, particularly THV 200, THV 300, THV 400, and THV 500. Preferred compositions include those which have a melting range between about 115° and 180° C. (by DSC), a melt flow index of 5 to 25 (ASTM 1238), a specific gravity of 1.95–1.98 g/cc (ASTM 792), and elongation at breakage of 500–600% (ASTM 638). Such polymeric compositions are shown, for other uses, in U.S. Pat. No. 4,991,932, U.S. Pat. No. 4,979,799, U.S. Pat. No. 4,986,630, to Herbrects et al; U.S. Pat. No. 4,829,116, and U.S. Pat. No. 4,556,589. The polymeric composition is preferably placed onto the catheter by first extruding the polymeric composition into suitably sized tubing, at least partially cross-linking the polymer (often using radiation such as electron beam), placing the polymer about the catheter, and heating the polymer to shrink it onto the catheter body.

In particular, we have found that extrusion of the composition is desirably accomplished using commercially available extruder equipment having, e.g., a 24:1 single screw head which has set up for tubing extrusion. For the catheter jacketing or sheathing, the tubing should be extruded with a wall thickness which ultimately (or as-installed on the catheter) is between about 0.0015 in. to 0.0035 in. with an inner diameter matching the outer diameter of the catheter section to be sheathed. Obviously, the physical size of the tubing upon extrusion will need be considered in view of the later processing steps which change that diameter. Extruder head temperatures for the preferred materials are preferably in the region of 370°–540° F. The tubing, after extrusion, is then irradiated by passing the tubing through an irradiation zone containing an electron beam (or other suitable radiation source) of about 15 to 40 MRads and then expanding the tubing, e.g., inflating with it air while heating the tubing. This expansion provides the tubing with biaxial elongation (both circumferential and lengthwise) and renders the tubing heat shrinkable. The expansion should be sufficient to produce a tubing which desirably is shrinkable by a factor of up to about 2.5 when shrunk onto the catheter body to form the sheathing.

Finally, the catheter (100) may be terminated with a proximal attachment (110) having a syringe sidearm and an electrical connector (112) for the electrodes (114).

Most of the configuration discussed herein, with the exception of that relating to the sensor section (102), is not critical to this invention and may be varied as needed to accommodate the concept of the presence of the sensor section (102).

Turning to FIG. 2, the sensor section (102) is shown in partial cutaway to show the general relationship of the sensors (114) to the remainder of the device. The most distal tip of distal section (104) is also shown. The wire tube (116) is generally made up of insulated conductors, each of which individually extends from the distal portion of the catheter assembly (100) to its proximal end. Each wire is insulated along its length but is stripped for contact and electrical joining with an electrical junction (112) at the proximal end of the catheter and for contact with an electrode (114) in the sensor section (102) of the catheter, by known techniques such as soldering, brazing, or welding. The tube of conductors preferably is woven, that is to say, that the conductors assume an in-and-out relationship with each other much in the same way that cloth is woven and pass in a spiral from the distal end of the tube to the proximal end of the tube. This weave may be regular, having each conductive filament trade inside for outside positions at every junction with a crossing conductor. The conductors may be grouped together in bundles or ribbons for multiple weaving. The weave may be the same configuration from distal to proximal end or it may be changed as desired from one end to the other to allow changes of flexibility or changes in overall diameter.

As discussed above in passing, the optional sheathing (119) is shown in the spaces between the electrodes (114) and in the gap between the distal section sheathing (117) and the most proximal electrode.

Although it is most desirable that the conductors be interwoven to form the regularly woven tube around the inner polymeric tubing (118), it is also within the purview of this invention that multiple conductors be merely twisted or flat-wound around the inner polymeric tubing (118) to form the tube of conductors. That is to say, an inner number of wires would be laid diagonally to the longitudinal axis of the inner polymeric tubing (118) and flat-wound spirally one way, e.g., clockwise or counterclockwise, around the tubing. An outer collection of conductor wires would be laid diagonally to the axis of the inner polymeric tubing (118) and flat-wound spirally or twisted in the opposite direction around the tubing and the inner layer of conductors.

Although a variety of conductive materials may be used as the conductive wires in this invention, e.g., metals such as silver, gold, platinum and copper, such materials are well known and a choice is well within skill of the designer in this art. We have found that typical electrical grade copper wires of a suitable diameter, e.g., 0.004 to 0.010 inches in diameter, is excellent and provides the necessary strength and flexibility for cardiac service.

The choice of electrical insulation for the wires is also within the scope of one having ordinary skill in this art. We have found that a variety of polyimide resins may be applied to the wires in a layer thin enough that the overall size of the resulting guidewire assembly is not excessive, the crosstalk between adjacent wires is very low, and the biocompatibility of the polymer is widely accepted. Polyethylene, polypropylene, polybutene, polyurethane, and mixtures and copolymers of these polymers are also quite suitable.

The minimum number of conductors in the wire tube is one. The remainder of the wires may be other filamentary material such as Dacron, silk, nylon, or other suitable material. Use of non-conductors retains the presence of the tube as a structural feature but minimizes the number of stiff wires in the tube if only a limited number of electrodes is needed in the sensor section.

The number of wires either woven into the tube or placed in the flat-wound variations may be as many as is desirable for the specific task involved as constrained by the necessary flexibility of the catheter. For instance, we have found that for 41 gauge copper wires (0.0066 inches in diameter) having a thin polyimide insulator coating, that tubes may be woven having 0.018 inch outside diameters with 16 independently monitorable electrodes at the distal tip. Obviously, with additional wires or using bundles of wires, the catheter assembly will be thicker and potentially less flexible. Nevertheless, it is within the scope of this invention that any reasonable number of woven or flat wound wires be utilized.

Guidewire Structure

Figure 3:
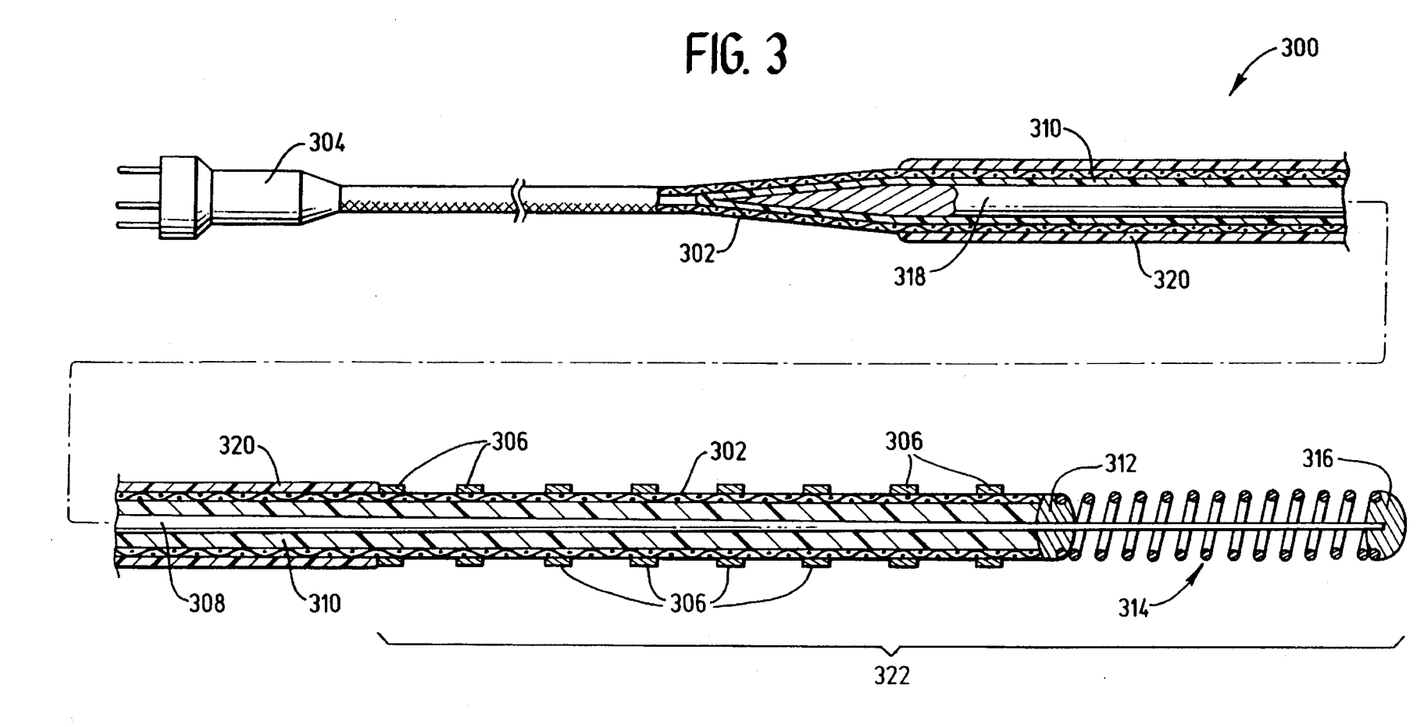
FIG. 3 is an enlarged cutaway side view of the inventive multipolar guidewire assembly.

FIG. 3 shows a partial cutaway side view of the inventive guidewire assembly (300). The guidewire itself is fairly flexible and is torqueable and often has an overall length between about 70 and about 300 cm between its proximal end and its distal end. The typical maximum outer diameter is often between 0.006 and 0.060, preferably between 0.010 and 0.040 inches. Although the diameter of the guidewire assembly may be constant along its length, more typically the diameter will range from a minimum of 0.015 to 0.020 inches at its distal end to 0.020 to 0.035 at its proximal.

As is the case with the wire tube discussed above, the guidewire is generally made up of a woven tube (302) comprising insulated conductors, each of which individually extends from the distal portion of the guidewire assembly to the proximal end of the guidewire assembly. Each wire or filament is insulated along its length but is stripped for contact and electrical joining with an electrical junction (304) at the proximal end of the guidewire assembly and for contact with an electrode (306) at the distal end of the guidewire assembly. The tube of conductors preferably is woven, that is to say, that the conductors assume an in-and-out relationship with each other much in the same way that cloth is woven and pass in a spiral from one end of the guidewire assembly to the other. This weave may be regular, having each conductive filament trade inside for outside positions at every junction with a crossing conductor. The conductors may be grouped together in bundles or ribbons for multiple weaving. The weave may be the same configuration from distal to proximal end or it may be changed as desired from one end to the other to allow changes of flexibility or changes in overall diameter.

Although it is most desirable that the conductors be interwoven to form the regularly woven tube, it is also within the purview of this invention that multiple conductors be merely twisted or wound around the core to form the tube of conductors. That is to say, an inner number of wires would be laid diagonally to the axis of the core and flat-wound spirally one way, e.g., clockwise or counterclockwise, around the core and the outer collection of conductor wires would be laid diagonally to the axis of the guidewire core and twisted in the opposite direction around the core and the inner layer of conductors. The nonwoven or wrapped guidewire is in many aspects not as desirable as the woven tube guidewire in that some method of having the various layers of wire adhere to each other is required, thereby potentially making the whole assembly somewhat stiffer. For the woven tube guidewire, the mechanical adhesion between the two sets of oppositely woven wires provides that necessary adhesion. The additional adhesive is not then necessary and allows the guidewire to maintain a high level of flexibility.

Although a variety of conductive materials may be used as the conductive wires in this invention, e.g., metals such as silver, gold, platinum and copper, such materials are well known and a choice is well within skill of the designer in this art. We have found that typical electrical grade copper wires of a suitable diameter, e.g., 0.004 to 0.010 inches in diameter, is excellent and provides the necessary strength and flexibility for cardiac service.

The choice of an insulating layer for the individual wires is also within the scope of one having ordinary skill in this art. We have found that a variety of polyimide resins may be applied to the wires in a layer thin enough that the overall size of the resulting guidewire assembly is not excessive, the crosstalk between adjacent wires is very low, and the biocompatibility of the polymer is widely accepted. Polyethylene, polypropylene, polybutene, polyurethane, and mixtures and copolymers of these polymers are also quite suitable.

The multifilament tubes (302), whether woven or flat wound, are typically placed over an insulated guidewire or core wire (308). Insulation (310) for the guidewire is also often desirable, although not absolutely necessary in many services because of the presence of the insulation upon the wires within the woven tube.

The core wire, at its distal end, passes through a junction at (312) which forms the end of the woven tube. The core wire passes through guide tip (314) and terminates at the guidewire terminator (316). The guide tip is typically of a material which is radiopaque, e.g., a noble metal such as platinum, rhodium, palladium or the like (although a platinum-tungsten alloy is preferred), so that it may be manipulated through the body's vasculature using x-rays.

Core wire (308) desirably has sections of differing flexibility and torqueability, e.g., at its more distal section it is thinner and consequently allows the resulting guidewire assembly to traverse through the diameters of the smaller veins and arteries. A suitable size for the core wire diameter in the region of electrodes (306) is 0.005 to 0.010 inches in diameter. In the most proximal section of the core wire (318), the core wire is desirably often larger so as to allow enhanced strength and to further allow transmittal of torque from the outside of the body towards the more distal portion of the guidewire as is the practice with using virtually any such guidewire. As is shown in FIG. 3, the core wire may be terminated in the region near the electrical junction (304) at the proximal ends so to simplify handling of the guidewire during its insertion and subsequent use. It is not obviously necessary that the core wire be terminated at that point but may instead be extended out through the electrical junction where such is a desirable design feature.

It is desirable to place an added layer of polymeric material (320) upon the outside of the woven tube (302). Although the insulation on the wires making up the woven tube is typically adequate for virtually any situation which may be encountered in the human body, the woven exterior of the tube has a corrugated or rough feel which sometimes complicates passage through the catheter body lumen. Consequently, covering (320) may desirably be a slippery material such as a fluorinated polymer, e.g., Teflon™, or other suitable lubricious polymer. Polyethylene, polypropylene, polybutene, polyurethane, and mixtures and copolymers of these polymers are also suitable. Hydrophilic polymers which are slippery when hydrated, such as polyvinylpyrrolidone, polyethylene oxide, or hyaluronic acid polymers are all excellent choices for such a covering.

It is desirable to cover or ensheath at least a portion of the guidewire with the fluoropolymeric composition (discussed above) comprising a copolymer of tetrafluoroethylene, hexafluoropropylene, and vinylidene fluoride or an alloy or mixture of the three. Especially suitable are the series of fluoroplastics known as "THV Fluoroplastics" by 3M, particularly THV 200, THV 300, THV 400, and THV 500. Such polymeric compositions are additionally shown, for other uses, in U.S. Pat Nos. 4,991,932, to Fitz et al; 4,979,799, to Herbrects et al; 4,986,630, to Herbrects et al; 4,829,116, to Piesold et al; and 4,556,589, to Neumann et al. Just as with the catheter body, the preferred procedure for placing the fluoroplastic sleeve onto the guidewire is by first extruding the polymeric composition into suitably sized tubing, at least partially cross-linking the polymer (often using radiation such as electron beam), biaxially stretching the tubing to allow it to be later shrunk-wrapped onto the guidewire, placing the polymer about the relevant portions of the guidewire, and heating the polymer to shrink it onto the guidewire.

The tubing used on the guidewire is produced in the same fashion as that used on the catheter and differs from that tubing usually only in the diameter of the tubing and in its wall thickness. The overall inner and outer diameters are chosen to conform to the size of the guidewire. In particular, the inner diameter as installed and shrunk onto the guidewire, is the same as the contiguous outer diameter of the guidewire. The outer diameter is as appropriate for the use but in the distal and sensor sections of the guidewire typically is the same as the outer diameter of the sensors (306). The wall is generally between 0.0005 in. and 0.0015 in. in thickness.

In addition, it may be desirable to incorporate compositions that evoke desired physiological responses into or onto the covering. For instance, anticoagulants and the like such as heparin and citric acid are desired additives to the covering.

Figure 4:
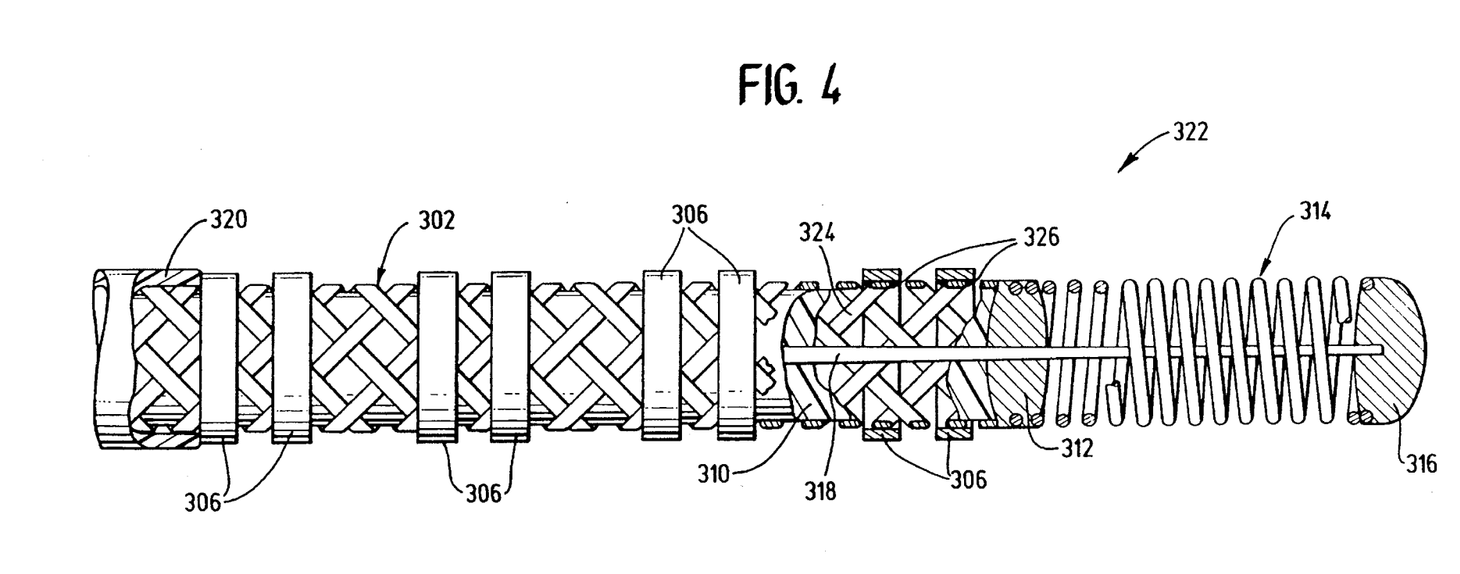
FIG. 4 is an enlarged side view of the distal section of the guidewire assembly.

The construction of the distal tip portion is more readily discussed referring to FIG. 4. FIG. 4 is a partial cutaway, side view, close up of the distal portion (322) of the catheter guidewire.

Shown in FIG. 3 is the coil guide tip (314), the guide tip terminator (316) and its more proximal junction (312). As was noted above, the coil guide tip (314) may be bent so to provide a ready manner to address branching veins or arteries in the event they need to be accessed during insertion of the inventive catheter assembly. The most distal eight contacts (306) of those found in the guidewire assembly shown in FIG. 3 are shown in FIG. 4. A cutaway is provided at the most distal of the two contacts (306), showing variously the insulation (310) and core wire (318). Further, the individually woven wires (324) on the back side of the assembly away from the viewer are also visible. Also shown in the cutaway are solder junctions (326) which join two of the wires (324) to the two most distal electrodes (306). Each of the electrodes has such a electrical joint joining it to one of the conductors found in the woven tube (302).

The contacts or electrodes are constructed of a material which does not easily corrode or oxidize when placed in communication with human body fluids. We have found that substantially pure gold serves such a purpose quite well and is easily soldered using biocompatible solder to the stripped wires found in the woven tube. The electrodes shown may be bands and desirably are 0.005 to 0.015 in width and of a suitable, mechanically stable thickness. The spacing of the bands along the axis of the guidewire assembly is a matter of design choice by the device designer. However, we have found that electrode widths of 0.10 inches with similar spacings between electrodes is adequate for most cardiac purposes. This spacing allows an adequate length of the guidewire to be placed within most of the smaller, but major, cardiac veins and arteries and allows a substantial mapping coverage.

The number of wires either woven into the tube or placed in the flat-wound variations may be as many as is desirable for the specific task involved as constrained by the necessary flexibility of the guidewire. For instance, We have found that for 41 gauge copper wires (0.0066 inches in diameter) having a thin polyimide insulator coating, that tubes may be woven having 0.018 inch outside diameters with 16 independently monitorable electrodes at the distal tip. Obviously, with additional wires or using bundles of wires, the catheter assembly will be thicker and potentially less flexible. Nevertheless, it is within the scope of this invention that any reasonable number of woven or flat wound wires be utilized.

Procedure

As has been noted before, it is highly desirable that the catheter assembly be used in the mapping of cardiac electrical activity, optionally with the multipole guidewire. With a reasonably sized guidewire such as that discussed above, a substantial portion of the major coronary arteries and veins may be accessed for electrical mapping and monitoring. It is further quite desirable that a number of the guidewires be used simultaneously in either or both of the coronary arteries and veins. Furthermore, the guidewire may be introduced into the vasculature into other regions of the human or animal body, such as the brain, to monitor the electrical activity there.

It should be apparent that the guidewire and the mapping catheter body may be used either in conjunction with each other or in isolation. The catheter may also be used to administer therapeutic and diagnostic agents with or without the inventive guidewire (or, indeed, any guidewire) in place.

Figure 5:
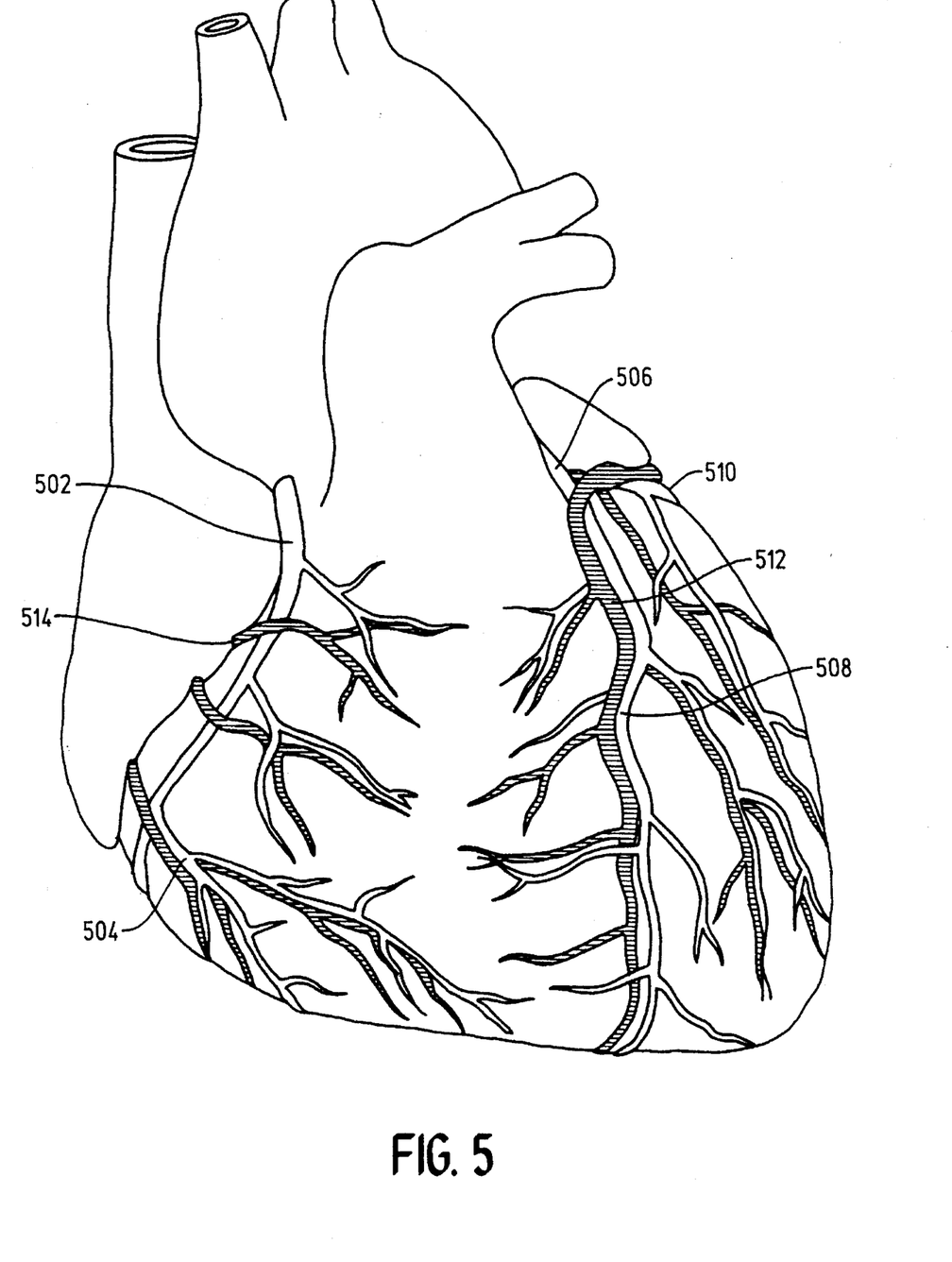
FIGS. 5 and 6 are anterior and posterior views of a human heart showing the major cardiac arteries and cardiac veins suitable for placement of the inventive guidewires and catheters as used for mapping cardiac activity according to the method of this invention.

FIG. 5 is an anterior view of the exterior of the human heart showing major coronary veins and arteries. Specific arteries which are of sufficient size to accept the mapping guidewires and catheters of the instant invention include the right coronary artery (502), the marginal artery (504), the left coronary artery (506), the anterior interventricular artery (508), and the circumflex artery (510). Similarly, specific veins visible in the depiction of FIG. 5 into which the inventive guidewire may be introduced include the great cardiac vein (512) and the anterior cardiac veins (514).

Figure 6:
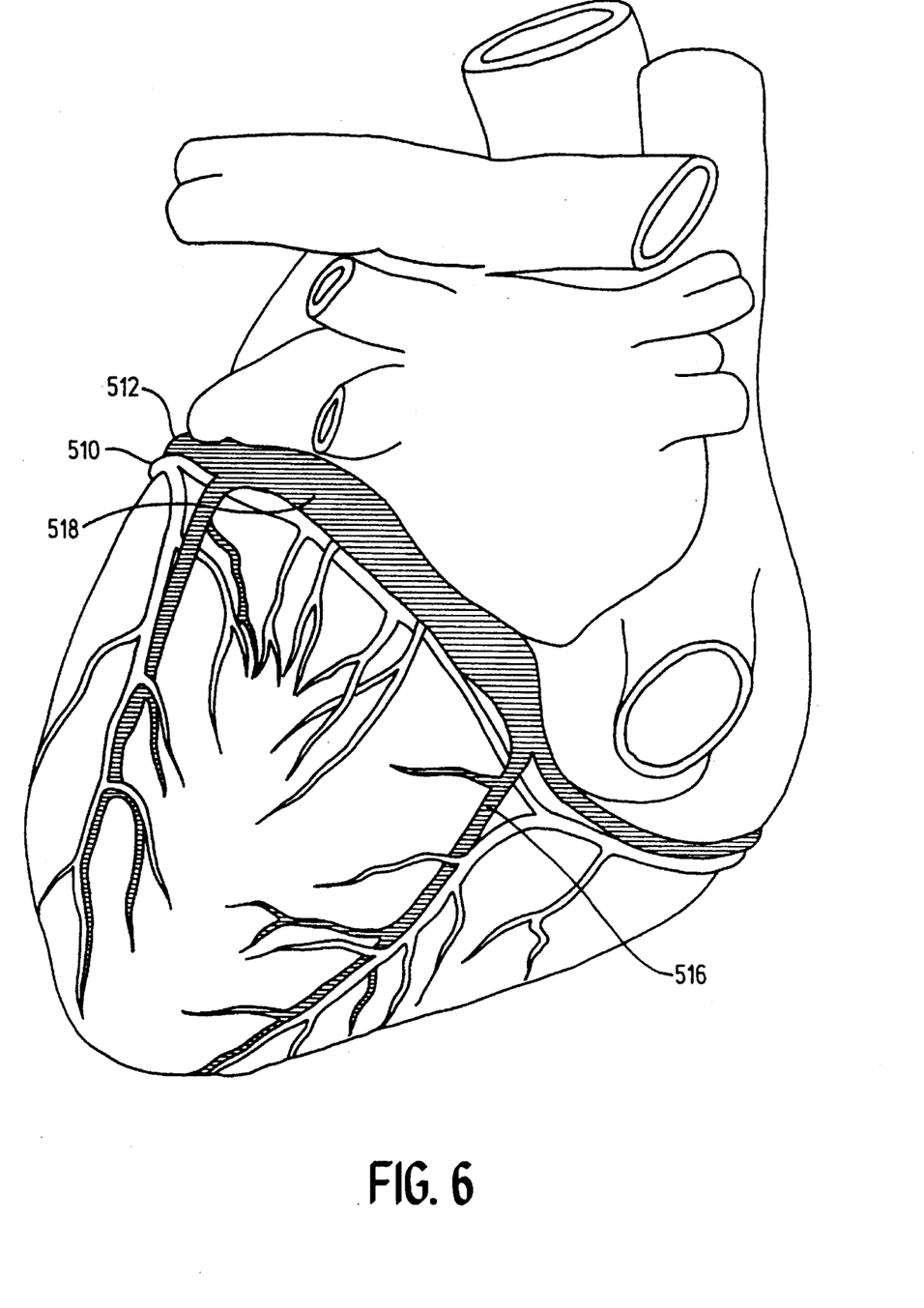

Similarly, in FIG. 6, which provides a posterior view of the human heart, the circumflex artery (510) is also visible. The middle cardiac vein (516) is visible and may be reached through the coronary sinus (518) and the great cardiac vein (512).

It is within the ambit of this invention that the catheter shown in FIG. 1, optionally with the guidewire shown in FIG. 3, be introduced into a femoral artery or a femoral vein (or other convenient body access site) and progressed through the body's vasculature to the coronary veins or arteries. Once the catheter is situated in the proper location in the coronary vasculature, a signal may be taken from the catheter and guidewire in any way that is appropriate for the specific indication. The catheter or guidewire may be moved to another location and a separate set of signals procured. It is, or should be, apparent that since each electrode found variously at the distal tip of the catheter (100) and the mapping guidewire (300) is individually brought out via the wires to the respective electrical connections at their proximal ends, that each electrode may be used in conjunction with any other electrode in any fashion considered appropriate. Similarly, the electrodes may be used in combination with external electrodes or leads.

In certain circumstances, the guidewires and catheters may be used in multiples, e.g., one guidewire in each of the major coronary veins and arteries shown in FIGS. 5 and 6 to provide an overall and complete electrical map of the heart. In this way, arrythymic foci may be readily located and therapeutic action taken.

EXAMPLE

A guidewire was constructed using a woven tubular braid of sixteen wires, eight woven counterclockwise and eight woven clockwise. Gold metal contacts of 0.100 inches width were attached at the distal end to eight of those wires at a distance of 0.050 inches apart. The catheter guidewire was 240 cm in length. An eight connector DIN plug was installed at the proximal end of the guidewire. The guidewire assembly was 0.018 inches in diameter at the distal end, 0.026 inches in diameter at the midsection, and 0.032 inches at the more proximal end.

The guidewire was introduced into the coronary artery of a live dog using a 7 French coronary guide catheter. A pacer lead having four electrodes was placed inside a heart chamber and was used to pace a ventricular beat so that the electrical activity produced as a result of that pacing could be monitored outside the heart chamber using the inventive mapping guidewire.

Figure 7:
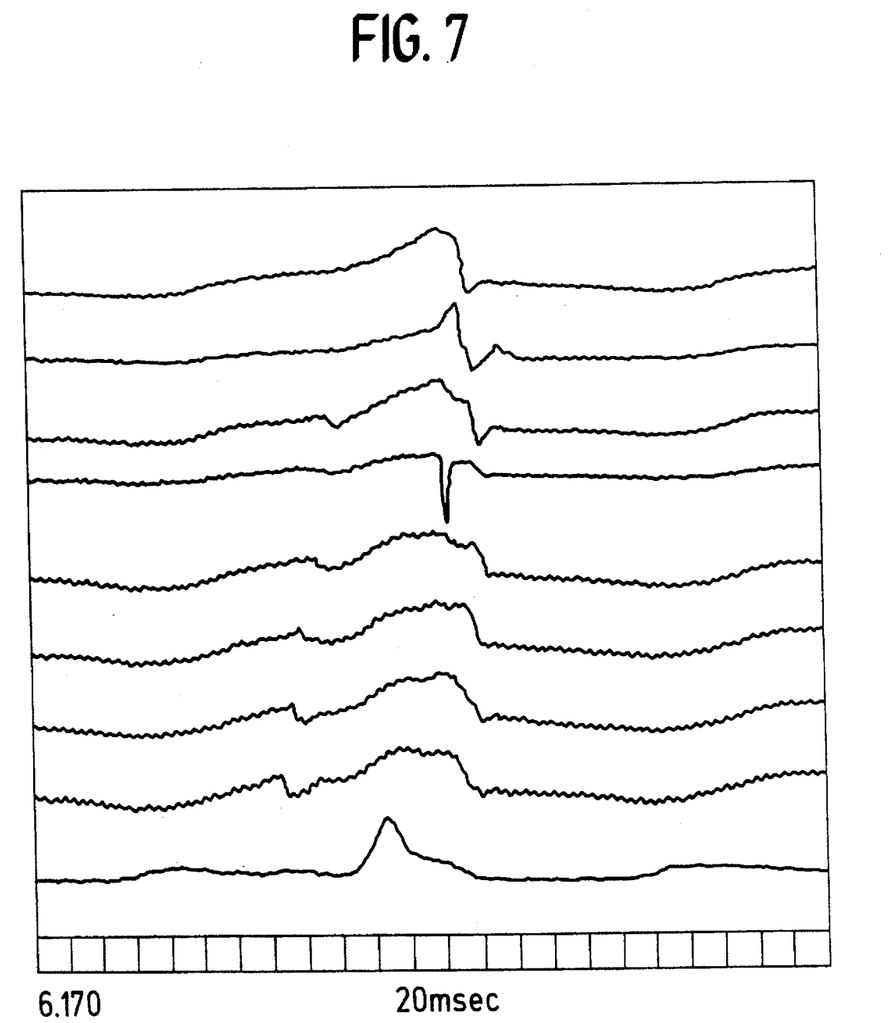
FIGS. 7, 8 and 9 are graphs of cardiac electrical activity made during an the experimental procedure.
Figure 8:
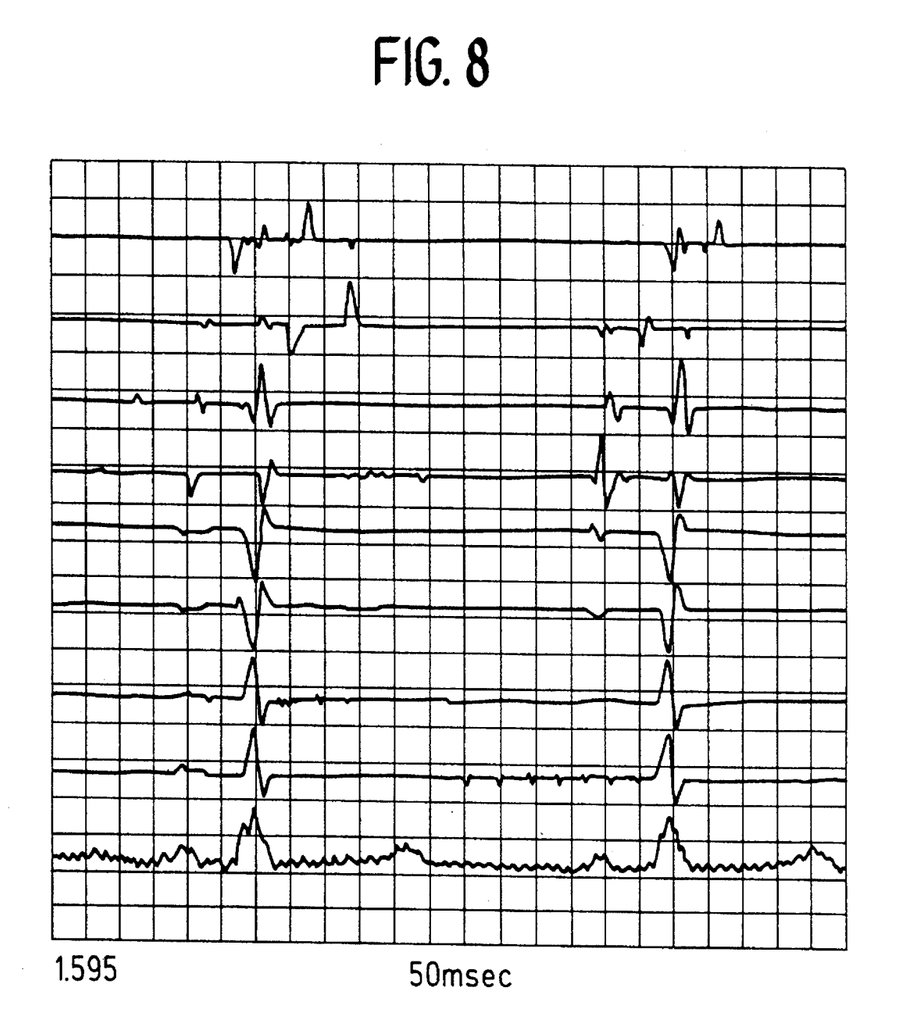
Figure 9:
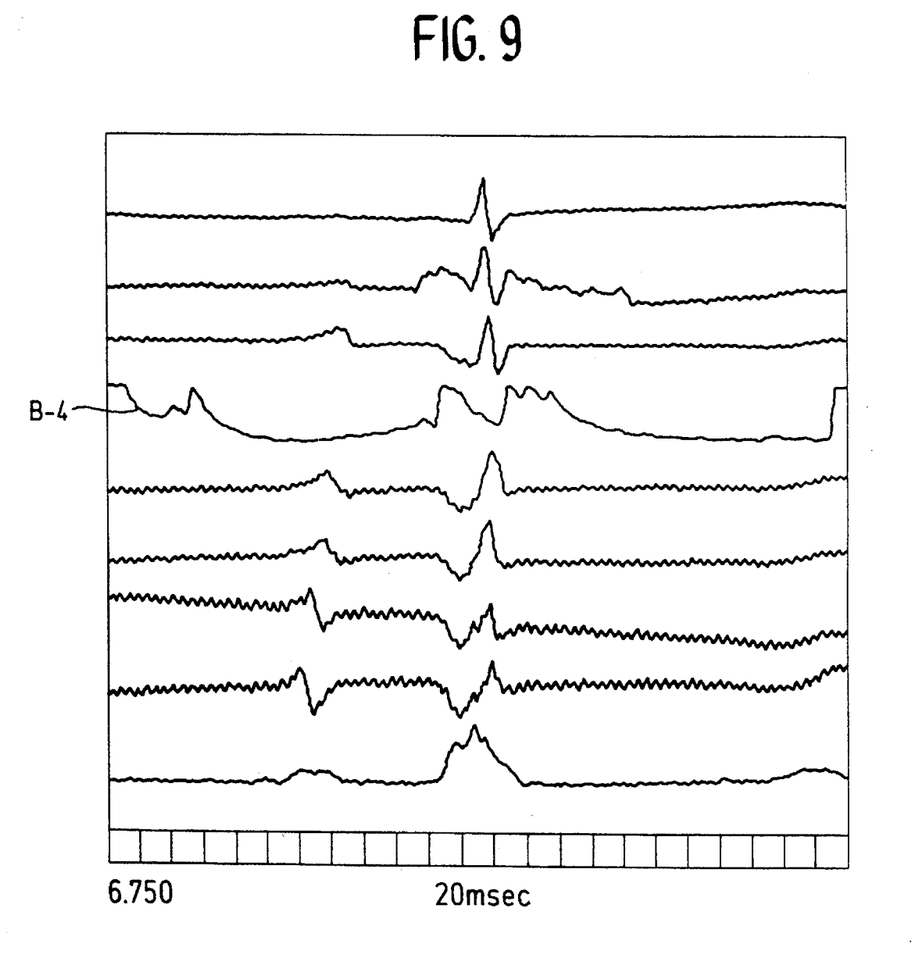

FIGS. 7, 8, and 9 are electrocardiograms produced using the catheter as described above. Each depicts one or two pulses from that animal test. FIG. 7 shows the signals obtained from the left coronary circumflex artery during a pacing pulse (shown on the bottom line of the graph). The guidewire electrodes were operated in unipolar mode.

FIGS. 8 and 9 show, respectively, two and one pulse from the left coronary circumflex artery during the sinus rhythm. FIG. 8 shows the guidewire operated in bipolar mode and FIG. 9 shows the guidewire operated in a unipolar mode. It may also be observed in FIG. 9 that the pulse intensifies in the B-4 trace thereby indicating that the pacing pulse was initiated in the heart chamber in the region of that electrode. This suggests that the guidewire may be used to locate the focus of arrythmia in the cardiac muscle for further treatment.

Although preferred embodiments of the present invention have been described, it should be understood that various changes, adaptations and modifications may be made therein without departing from the spirit of the invention and the scope of the claims which follow.

We claim as our invention:

1. A multipolar sensing catheter having a distal end, a proximal end and a longitudinal axis comprising:

a tubular shaft having an outer surface and an inner lumen extending therein and formed at least in part by a plurality of filaments, at least one of which is an insulated electrical conductor, each such insulated electrical conductor extending from a distal portion of the catheter to the proximal end thereof, and a fluoropolymeric sheath comprising tetrafluoroethylene, hexafluoropropylene, and vinylidene fluoride forming at least in part the outer surface of the catheter shaft, and at least one electrode pair situated in a distal portion of the catheter, each electrode of said at least one electrode pair being electrically connected to a separate insulated electrical conductor.

2. The catheter of claim 1 including at least one additional electrode pair on the distal portion which is spaced apart from the other electrode pair along the longitudinal axis of the catheter with each electrode of said additional electrode pair being electrically connected to a separate insulated electrical conductor.

3. The catheter of claim 1 additionally comprising a stiff catheter proximal portion, a comparatively less stiff catheter mid portion located distal of the catheter proximal portion, and a comparatively least stiff catheter distal section located distal of the catheter mid portion and proximal of the sensor section.

4. The catheter of claim 1 additionally comprising a guidewire slidably disposed within the inner lumen of the tubular shaft.

5. The catheter of claim 4 where the guidewire is a multipolar sensing guidewire having a distal end, a proximal end, and a longitudinal axis comprising:

an outer guidewire tube having an inner lumen formed at least in part of a plurality of insulated conductors extending from a distal portion of the guidewire to the proximal end of the guidewire, a plurality of electrodes on the distal portion of the guidewire which are spaced apart from each other along the longitudinal axis of the guidewire and which are individually electrically connected to an insulated electrical conductor, and a core member disposed within the inner lumen of the outer guidewire tube extending from the distal portion of the guidewire to the proximal end of the guidewire.

6. The catheter of claim 5 where the plurality of insulated electrical conductors in the guidewire are woven to form the outer tube.

7. The catheter of claim 5 where the plurality of insulated electrical conductors in the guidewire are spirally wound around said core member.

8. The catheter of claim 5 wherein the guidewire includes an electrical connector at the proximal end of the guidewire which is electrically connected to the electrical conductors forming at least in part the outer guidewire tube.

9. The catheter of claim 5 wherein the guidewire also includes a coil distal tip secured to the core member extending within the inner lumen of the guidewire tube.

10. The catheter of claim 5 wherein the outer tube of the guidewire an exterior coating which extends from the proximal end of the guidewire to a location distal to the electrodes.

11. The catheter of claim 9 wherein the outer tube of the guidewire has an exterior surface formed at least in part by a polymer material which is selected from the group consisting of fluorinated polymers, polyethylene, polypropylene, polybutene polyurethane, polyvinylpyrrolidone, polyethylene oxide, hyaluronic acid polymers and mixtures and copolymers thereof.

12. The catheter of claim 11 in which the fluorinated polymers are selected from the group consisting of a copolymer, a mixture and an alloy of tetrafluoroethylene, hexafluoropropylene and vinylidene fluoride.

13. In an intravascular assembly comprising a catheter having an inner lumen extending therein and a multipolar sensing guidewire slidably disposed within the inner lumen, the guidewire having a distal end, a proximal end, and a longitudinal axis;

an outer tube formed at least in part of a plurality of insulated electrical conductors extending from a distal section to a proximal section of the guidewire and having an outer fluoropolymeric coating covering a portion of an exterior surface of the outer tube comprising tetrafluoroethylene, hexafluoropropylene, and vinylidene fluoride;

a plurality of electrodes on the distal section of the guidewire which are spaced apart from each other along the guidewire axis and which are electrically connected to individual insulated electrical conductors, and a core member within an inner lumen defined by the outer tube of the guidewire extending through the proximal and distal sections of the guidewire.

14. The catheter of claim 13 wherein the plurality of insulated electrical conductors in the guidewire are woven to form the outer tube of the guidewire.

15. The catheter of claim 13 wherein the plurality of insulated electrical conductors in the guidewire are wound spirally around said core member.

16. The catheter of claim 13 wherein the guidewire has an electrical junction at its proximal end which is electrically connected to electrical conductors forming at least in part the outer tube of the guidewire.

17. The catheter of claim 13 wherein the guidewire includes a coil distal tip secured to the core member.

18. A multipolar sensing guidewire having a distal end, a proximal end, and a longitudinal axis;

an outer tube formed at least in part of a plurality of insulated electrical conductors extending from a distal section to a proximal section of the guidewire and having an outer fluoropolymeric coating comprising tetrafluoroethylene, hexafluoropropylene, and vinylidene fluoride which covers at least a portion of the outer tube, a plurality of electrodes on a distal section of the guidewire which are spaced apart from each other along the guidewire axis and which are electrically connected to individual insulated electrical conductors, and a core member within an inner lumen defined by the outer tube of the guidewire extending through the proximal and distal sections of the guidewire.

19. The guidewire of claim 18 where the plurality of insulated electrical conductors are woven to form the outer tube.

20. The guidewire of claim 13 where the plurality of the insulated electrical conductors are wound spirally around said core member.

21. The guidewire of claim 13 including a coil distal tip secured to the core member.

22. An elongated intravascular device for detecting electrical activity within a body lumen of a patient, comprising:

a) an elongated tubular shaft having proximal and distal shaft sections;

b) a plurality of sensing electrodes mounted on the distal shaft section;

c) a tubular member within the elongated tubular shaft which is formed from a plurality of individually insulated electrical conductors with each sensing electrode being electrically connected to a separate electrical conductor; and d) an outer fluoropolymeric coating covering at least part of the tubular member comprising tetrafluoroethylene, hexafluoropropylene and vinylidene fluoride.

23. The elongated intravascular device of claim 22 wherein the tubular member is formed of braided electrical conductors.

* * * * *

UNITED STATES PATENT AND TRADEMARK OFFICE
CERTIFICATE OF CORRECTION

PATENT NO. : 5,549,109
DATED : August 27, 1996
INVENTOR(S) : G. Samson et al.

It is certified that error appears in the above-indentified patent and that said Letters Patent is hereby corrected as shown below:

Column 15, line 23, change "13" to --18--; and

Column 16, line 1, change "13" to --18--.

Signed and Sealed this

Thirtieth Day of September, 1997

Attest:

BRUCE LEHMAN

Attesting Officer

Commissioner of Patents and Trademarks